United States Patent
Zhuang et al.

(10) Patent No.: US 12,232,497 B2
(45) Date of Patent: Feb. 25, 2025

(54) MIXED BACTERIA FOR PROMOTING NODULATION AND NITROGEN FIXATION OF ROBINIA PSEUDOACACIA AND APPLICATION THEREOF

(71) Applicant: NANJING FORESTRY UNIVERSITY, Nanjing (CN)

(72) Inventors: Jiayao Zhuang, Nanjing (CN); Chao Liu, Nanjing (CN); Xiaoxue Wang, Nanjing (CN); Jiaxin Zheng, Nanjing (CN); Kun Tian, Nanjing (CN)

(73) Assignee: NANJING FORESTRY UNIVERSITY, Nanjing (CN)

( * ) Notice: Subject to any disclaimer, the term of this patent is extended or adjusted under 35 U.S.C. 154(b) by 121 days.

(21) Appl. No.: 17/147,173

(22) Filed: Jan. 12, 2021

(65) Prior Publication Data
US 2024/0196904 A1    Jun. 20, 2024

Related U.S. Application Data

(63) Continuation of application No. PCT/CN2020/113434, filed on Sep. 4, 2020.

(30) Foreign Application Priority Data

Sep. 29, 2019 (CN) .......................... 2019109381957

(51) Int. Cl.
| | |
|---|---|
| *A01N 63/22* | (2020.01) |
| *A01N 25/02* | (2006.01) |
| *C12N 1/20* | (2006.01) |
| *C12R 1/07* | (2006.01) |

(52) U.S. Cl.
CPC ............ *A01N 63/22* (2020.01); *A01N 25/02* (2013.01); *C12N 1/205* (2021.05); *C12N 2500/12* (2013.01); *C12N 2500/74* (2013.01); *C12N 2501/998* (2013.01); *C12N 2523/00* (2013.01); *C12N 2527/00* (2013.01); *C12R 2001/07* (2021.05)

(58) Field of Classification Search
CPC ...................................................... A01N 63/22
See application file for complete search history.

(56) References Cited

U.S. PATENT DOCUMENTS

| | | | | |
|---|---|---|---|---|
| 2005/0217174 | A1* | 10/2005 | Angle ...................... | A01H 3/00 |
| | | | | 47/58.1 R |
| 2024/0196904 | A1* | 6/2024 | Zhuang ................... | C05G 3/90 |

FOREIGN PATENT DOCUMENTS

CN    105754607 A  *  7/2016

* cited by examiner

*Primary Examiner* — Gina C Justice
(74) *Attorney, Agent, or Firm* — Bayramoglu Law Offices LLC

(57) ABSTRACT

A mixed bacteria for promoting nodulation and nitrogen fixation of *Robinia pseudoacacia* and their application are provided. The mixed bacteria includes *Kocuria* sp. X-22, *Microbacterium* sp. X-26, and *Bacillus* sp. X-28, all of which have been preserved in China Center for Type Culture Collection, and the preservation numbers respectively are: CCTCC No: M 2019237; CCTCC No: M 2019238; CCTCC No: M 2019239. The mixed bacteria are watered directly around the seedlings of *Robinia pseudoacacia*. Compared with the single bacteria control group and the sterile control group, the disclosure can produce synergistic superimposing effects, significantly improve the nodulation rate and symbiotic nitrogen fixation of the *Robinia pseudoacacia*, and promote the photosynthesis of the *Robinia pseudoacacia*.

8 Claims, 1 Drawing Sheet
Specification includes a Sequence Listing.

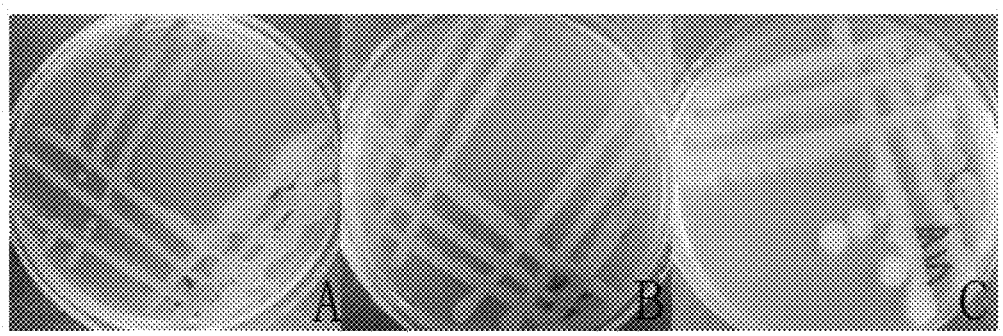

SEQUENCE LISTING

```
<160> NUMBER OF SEQ ID NOS: 3

<210> SEQ ID NO 1
<211> LENGTH: 1080
<212> TYPE: DNA
<213> ORGANISM: Artificial Sequence
<220> FEATURE:
<223> OTHER INFORMATION: Kocuria sp

<400> SEQUENCE: 1
cggaagtggc ggcgtgctta cacatgcagt cgaacgatga tgcccagctt gctgggcgga      60
ttagtggcga acgggtgagt aatacgtgag taacctgccc ttgactctgg gataagcctg     120
ggaaactggg tctaatactg gatactacct cttaccgcat ggtgggtggt ggaaagggtt     180
ttactggttt tggatgggct cacggcctat cagcttgttg gtggggtaat ggctcaccaa     240
ggcgacgacg ggtagccggc ctgagagggt gaccggccac actgggactg agacacggcc     300
cagactccta cgggaggcag cagtgggaa tattgcacaa tgggcggaag cctgatgcag     360
cgacgccgcg tgagggatga cggccttcgg gttgtaaacc tctttcagta gggaagaagc     420
gagagtgacg gtacctgcag aagaagcgcc ggctaactac gtgccagcag ccgcggtaat     480
acgtagggcg caagcgttgt ccggaattat tgggcgtaaa gagctcgtag gcggtttgtc     540
gcgtctgctg tgaaagcccg gggctcaacc ccgggtctgc agtgggtacg ggcagactag     600
agtgcagtag gggagactgg aattcctggt gtagcggtga aatgcgcaga tatcaggagg     660
aacaccgatg gcgaaggcag gtctctgggc tgttactgac gctgaggagc gaaagcatgg     720
ggagcgaaca ggattagata ccctggtagt ccatgccgta aacgttgggc actaggtgtg     780
ggggacattc cacgttttcc gcgccgtagc taacgcatta agtgccccgc ctggggagta     840
cggccgcaag gctaaaactc aaaggaattg acggggccc gcacaagcgg cggagcatgc     900
ggattaattc gatgcaacgc gaagaacctt accaaggctt gacattcacg gaccgcccca     960
gagatggggt tcccttcggg ctggtggaca ggtggtgcat gatgtcgtca gctcgtgtcg    1020
tgaaaatgtg gtaagtcccg cacgagcgca accctcgttc tatgttgcag acacgtgatg    1080
```

<210> SEQ ID NO 2
<211> LENGTH: 1080
<212> TYPE: DNA
<213> ORGANISM: Artificial Sequence
<220> FEATURE:
<223> OTHER INFORMATION: Microbacterium sp.

<400> SEQUENCE: 2

| | | | | | |
|---|---|---|---|---|---|
| gggcgattgg | gcggcgtgct | tacacatgca | gtcgaacgat | gaagcccagc | ttgctgggtg | 60 |
| gattagtggc | gaacgggtga | gtaacacgtg | agcaacctgc | ccctgactct | gggataagcg | 120 |
| ctggaaacgg | cgtctaatac | tggatatgtc | ccgtcaccgc | atggtgtgcg | ggtggaaaga | 180 |
| tttttcggtt | ggggatgggc | tcgcggccta | tcagcttgtt | ggtgaggtaa | tggctcacca | 240 |
| aggcgtcgac | gggtagccgg | cctgagaggg | tgaccggcca | cactgggact | gagacacggc | 300 |
| ccagactcct | acgggaggca | gcagtgggga | atattgcaca | atgggcggaa | gcctgatgca | 360 |
| gcaacgccgc | gtgagggatg | acggccttcg | ggttgtaaac | ctcttttagc | agggaagaag | 420 |
| cgagagtgac | ggtacctgca | gaaaaagcac | cggctaacta | cgtgccagca | gccgcggtaa | 480 |
| tacgtagggt | gcaagcgtta | tccggaatta | ttgggcgtaa | agagctcgta | ggcggtctgt | 540 |
| cgcgtctgct | gtgaaatccc | gaggctcaac | ctcgggcttg | cagtgggtac | gggcagacta | 600 |
| gagtgcggta | ggggagattg | gaattcctgg | tgtagcggtg | gaatgcgcag | atatcaggag | 660 |
| gaacaccgat | ggcgaaggca | gatctctggg | ccgtaactga | cgctgaggag | cgaaagggtg | 720 |
| gggagcaaac | aggcttagat | accctggtag | tccacccgt | aaacgttggg | aactagttgt | 780 |
| ggggtccttt | ccacggattc | cgtgacgcag | ctaacgcatt | aagttccccg | cctggggagt | 840 |
| acggccgcaa | ggctaaaact | caaaggaatt | gacgggggacc | cgcacaagcg | gcggagcatg | 900 |
| cggattaatt | cgatgcaacg | cgaagacctt | accaaggctg | acttacacga | gacgggccag | 960 |
| aaatggtcac | tctttggaca | cctcgtgaac | aggtggtgca | tgctgtcgtc | agctcgtgtc | 1020 |
| tggaatgtga | taagttcccg | cacgagcgca | ccctcgttct | atgtggcaga | cacgtaattg | 1080 |

<210> SEQ ID NO 3
<211> LENGTH: 1053
<212> TYPE: DNA
<213> ORGANISM: Artificial Sequence
<220> FEATURE:
<223> OTHER INFORMATION: Bacillus sp.

<400> SEQUENCE: 3

| | | | | | |
|---|---|---|---|---|---|
| atggccgtgg | cggcgtgcta | tacatgcaag | tcgagcgaac | tgattagaag | cttgcttcta | 60 |
| tgacgttagc | ggcggacggg | tgagtaacac | gtgggcaacc | tgcctgtaag | actgggataa | 120 |
| cttcgggaaa | ccgaagctaa | taccggatag | gatcttctcc | ttcatgggag | atgattgaaa | 180 |
| gatggtttcg | gctatcactt | acagatgggc | ccgcggtgca | ttagctagtt | ggtgaggtaa | 240 |
| cggctcacca | aggcaacgat | gcatagccga | cctgagaggg | tgatcggcca | cactgggact | 300 |
| gagacacggc | ccagactcct | acgggaggca | gcagtaggga | atcttccgca | atggacgaaa | 360 |
| gtctgacgga | gcaacgccgc | gtgagtgatg | aaggctttcg | ggtcgtaaaa | ctctgttgtt | 420 |
| agggaagaac | aagtacgaga | gtaactgctc | gtaccttgac | ggtacctaac | cagaaagcca | 480 |
| cggctaacta | cgtgccagca | gccgcggtaa | tacgtaggtg | gcaagcgtta | tccggaatta | 540 |
| ttgggcgtaa | agcgcgcgca | ggcggttct | taagtctgat | gtgaaagccc | acggctcaac | 600 |
| cgtggagggt | cattggaaac | tgggaacttg | agtgcagaa | gagaaaagcg | gaattccacg | 660 |

-continued

```
tgtagcggtg aaatgcgtag agatgtggag gaacaccagt ggcgaaggcg gcttttggt      720 ctgtaactga cgctgaggcg cgaaagcgtg gggagcaaac aggattagat accctggtag      780
tccacgccgt aaacgatgag tgctaagtgt tagagggttt ccgcccttta gtgctgcagc      840
taacgcatta agcactccgc ctggggagta cggtcgcaag actgaaactc aaggattgac      900
gggggcccgc acagcggtga gcatgtgttt aattcgaagc aacgcgaaga acttaccagt      960
ctgacatctc tgacactcta gagatagacg tcctctcggg acgagtgaca ggtggtgcat     1020
gatgtcgtca gctcgtgtct gaaaatgtgg gta                                  1053
```

MIXED BACTERIA FOR PROMOTING NODULATION AND NITROGEN FIXATION OF ROBINIA PSEUDOACACIA AND APPLICATION THEREOF

REFERENCE TO SEQUENCE LISTING

The substitute sequence listing is submitted as an ASCII formatted text filed via EFS-Web, with a file name of "Substitute_Sequence_Listing_GLP_US_SJDL041.TXT", a creation date of Dec. 27, 2022, and a size of 4913 bytes. The substitute sequence Listing filed via EFS-Web is a part of the specification and is incorporated in its entirety by reference herein.

TECHNICAL FIELD

The present disclosure relates to the technical field of microorganisms, and more specifically, to a kind of mixed bacteria for promoting nodulation and nitrogen fixation of *Robinia pseudoacacia* and it's application.

BACKGROUND

External-soil spray seeding is a greening technology in which a mixture of soil growth substrate materials and plant seeds are sprayed on the rocky soil slope evenly and at high pressure. The growth substrate material mixture of this technology is prepared with well-selected soil bacteria, which is mainly a greening technology developed for hard slopes such as rocks and for plants to create a suitable growth environment on hard slopes. As one of the important components of the growth substrate material of this technology, the selected soil bacteria play two roles: firstly, it can respond to changes in soil ecological mechanism and environmental stress, accelerate rock erosion, and effectively improve the fusion of the rock wall and the spray seeding substrate interface; secondly, it is to promote the growth and development of plants to ensure the supply of nutrients such as carbon and nitrogen in the stress environment. However, in actual engineering, the use of this technology is subject to many restrictions. On the one hand, the spray seeding substrate is difficult to maintain on the rock surface for a long time. On the other hand, the discovery of soil microorganisms that can promote growth of spraying tree species is rare.

During their life activities, soil microorganisms convert inert nitrogen in the air into ionic nitrogen that can be directly absorbed by vegetation to ensure the nitrogen nutrition of vegetation. At the same time, the stomatal conductance of vegetation treated by microorganisms with a growth-promoting effect can be increased, which can accelerate the gas exchange of plant cells, and increase the intercellular $CO_2$ concentration, so that the $CO_2$ required for photosynthesis is sufficient, which further improves the photosynthetic rate of plants and promotes the photosynthesis. In addition, microorganisms can decompose incompatible minerals in the soil and degrade inorganic and organic pollutants during their life activities. These all ensure the supply of nutrients required by vegetation in the microenvironment and the normal progress of life activities of vegetation. Therefore, the obvious and targeted selection of growth-promoting bacteria for specific vegetation is one of the keys to the wide application of the external-soil spray seeding greening technology. At present, there are few reports on the selection of suitable legume vegetation nodule-promoting strains for different vegetations in China.

SUMMARY

In view of the shortcomings in the prior art, the technical problem to be solved by the present disclosure is to select suitable leguminous vegetation nodule-promoting strains, and provide a kind of mixed bacteria for promoting nodulation and nitrogen fixation of *Robinia pseudoacacia*, which provides strain support for the establishment of the growth-promoting bacteria library of the spray seeding substrate. Another object of the present disclosure is to provide the application of the mixed bacteria in promoting nodulation and nitrogen fixation of *Robinia pseudoacacia*. It can produce a synergistic additive effect, provide high levels of nitrogen, and promote the nodulation and nitrogen fixation of *Robinia pseudoacacia*. Another object of the present invention is to provide the application of the mixed bacteria in promoting growth of *Robinia pseudoacacia*. Each growth index has a certain growth, and the growth is good.

Technical solution: In order to solve the above technical problems, the technical solutions adopted by the present disclosure are as follows:

A mixed bacteria for promoting nodulation and nitrogen fixation of *Robinia pseudoacacia* including *Kocuria* sp. X-22, *Microbacterium* sp. X-26, and *Bacillus* sp. X-28 is provided.

The *Kocuria* sp. X-22 is preserved in China Center for Type Culture Collection, the preservation date is Apr. 8, 2019, the preservation number is CCTCC No: M 2019237, and the preservation address is Wuhan University, Wuhan, China. The deposit was made under the Budapest Treaty, and all restrictions on the availability to the public of the deposited material will be irrevocably removed upon the granting of the patent.

The *Microbacterium* sp. X-26 is preserved in China Center for Type Culture Collection, the preservation date is Apr. 8, 2019, the preservation number is CCTCC No: M 2019238, and the preservation address is Wuhan University, Wuhan, China. The deposit was made under the Budapest Treaty, and all restrictions on the availability to the public of the deposited material will be irrevocably removed upon the granting of the patent.

The *Bacillus* sp. X-28 is preserved in China Center for Type Culture Collection, the preservation date is Apr. 8, 2019, the preservation number is CCTCC No: M 2019239, and the preservation address is Wuhan University, Wuhan, China. The deposit was made under the Budapest Treaty, and all restrictions on the availability to the public of the deposited material will be irrevocably removed upon the granting of the patent.

An application of the mixed bacteria in promoting nodulation and nitrogen fixation of *Robinia pseudoacacia*.

In the above-mentioned application, the mixed bacteria are respectively prepared into fermentation broths, and the respective fermentation broths are diluted and mixed and then directly watered on the rhizosphere soil of *Robinia pseudoacacia* seedlings.

In the above-mentioned application, preparation methods of the fermentation broth are:
1) Preparing strains of *Kocuria* sp. X-22, *Microbacterium* sp. X-26, and *Bacillus* sp. X-28, and activating the prepared strains on a nutrient agar solid medium at 35° C. for 24 hours;
2) picking up a loop of bacterial paste of the activated *Microbacterium* sp. X-26 and *Bacillus* sp. X-28 strains with an inoculation loop, adding the bacterial paste to the LB liquid medium, adding the bacterial paste to the LB liquid medium respectively, inoculating *Kocuria* sp. X-22 into NA liquid medium, and shaking the mediums at a constant temperature of 35° C., a frequency of 200 r/min, for 24 hours to prepare a seed solution;

3) taking the seed solution with 3% of the inoculum amount, inoculating the taken seed solution into liquid medium, and culturing with shaking at a temperature of 35° C., a frequency of 200 r/min, for 36 hours to obtain the fermentation broth;

4) Before use, diluting the fermentation broth obtained in step 3) with sterile water, and then mixing in an equal volume for use.

The liquid medium in step 3) is 10 g peptone, 3 g yeast powder, 5 g sodium chloride, and 1000 mL sterile water, with pH 5.6.

An application of the mixed bacteria in promoting growth of *Robinia pseudoacacia*.

In the above-mentioned application, the mixed bacteria are respectively prepared into fermentation broths, and the respective fermentation broths are diluted and mixed and then directly watered on the rhizosphere soil of *Robinia pseudoacacia* seedlings.

In the above-mentioned application, a preparation method of fermentation broth is:

1) Preparing strains of *Kocuria* sp. X-22, *Microbacterium* sp. X-26, and *Bacillus* sp. X-28, and activating the prepared strains on a nutrient agar solid medium at 35° C. for 24 hours;

2) picking up a loop of bacterial paste of the activated *Microbacterium* sp. X-26 and *Bacillus* sp. X-28 strains with an inoculation loop, adding the bacterial paste to the LB liquid medium respectively, inoculating *Kocuria* sp. X-22 into NA liquid medium, and shaking the mediums at a constant temperature of 35° C., a frequency of 200 r/min, for 24 hours to prepare a seed solution;

3) taking the seed solution with 3% of the inoculum amount, inoculating the taken seed solution into liquid medium, and culturing with shaking at a temperature of 35° C., a frequency of 200 r/min, for 36 hours to obtain the fermentation broth;

4) diluting the fermentation broth obtained in step 3) with sterile water, and then mixing in an equal volume for use.

The liquid medium in step 3) is 10 g peptone, 3 g yeast powder, 5 g sodium chloride, and 1000 mL sterile water, with pH 5.6.

Beneficial effects: Compared with the prior art, the present disclosure selected and identified *Kocuria* sp. X-22, *Microbacterium* sp. X-26, and *Bacillus* sp. X-28. These three strains were activated and cultured with shaking to obtain the fermentation broth.

After the fermentation bacteria liquid is diluted and mixed in equal proportions, the applied bacteria liquid is obtained and applied to the planted *Robinia pseudoacacia* seedlings, which can produce a synergistic superimposing effect, significantly increase the nodulation rate of the *Robinia pseudoacacia* and the level of symbiotic nitrogen fixation, promote the photosynthesis of the *Robinia pseudoacacia*, and provide a new choice for spraying substrate growth-promoting bacteria.

BRIEF DESCRIPTION OF THE DRAWINGS

FIG. 1 is a diagram of the colonies of *Kocuria* sp. X-22, *Microbacterium* sp. X-26, and *Bacillus* sp. X-28 on a nutrient agar solid medium; in the figure, A: *Kocuria* sp. X-22; B: *Microbacterium* sp. X-26; C: *Bacillus* sp. X-28.

DETAILED DESCRIPTION OF EMBODIMENTS

The present disclosure will be further described below in conjunction with specific embodiments, but these embodiments are not used to limit the present disclosure. The methods used in the following embodiments are conventional methods unless otherwise specified.

Embodiment 1

1) Acquisition and Identification of Strain

Soil samples were collected from the 5 cm rhizosphere soil on the slopes on both sides of Yueyang Avenue in Yueyang City. The dilution coating plate method is adopted. In a 35° C. incubator, it was cultured on a nutrient agar solid medium (NA medium: peptone 10 g; beef powder 3 g; sodium chloride 5 g; agar 15 g; sterile water 1000 mL) for 2 to 3 days. Different colonies were picked out by naked eye observation, and several different species of single colonies were obtained through repeated streaking and purification.

A single colony was selected and made into a plate, and was sent to Shanghai Jinyu Medical Laboratory for sequencing, and the 16S rDNA gene sequence was obtained, as shown in SEQ ID NO. 1. The detected 16S rDNA gene sequence was BLAST aligned with the sequence in the GenBank database. The results showed that the similarity between this strain and *Kocuria polaris* was 99.32%. The morphological characteristics and 16S rDNA gene sequence were combined and analyzed, and it was identified as *Kocuria* sp. X-22.

Another single colony was selected and made into a plate, and was sent to Shanghai Jinyu Medical Laboratory for sequencing, and the 16S rDNA gene sequence was obtained, as shown in SEQ ID NO. 2. The detected 16S rDNA gene sequence was BLAST aligned with the sequence in the GenBank database. The results showed that the similarity between this strain and *Microbacterium arabinogalactanolyticum* was 98.91%. The morphological characteristics and 16S rDNA gene sequence were combined and analyzed, and it was identified as *Microbacterium* sp. X-26.

Still another single colony was selected and made into a plate, and was sent to Shanghai Jinyu Medical Laboratory for sequencing, and the 16S rDNA gene sequence was obtained, as shown in SEQ ID NO. 3. The detected 16S rDNA gene sequence was BLAST aligned with the sequence in the GenBank database. The results showed that the similarity between this strain and *Bacillus megaterium* was 99.70%. The morphological characteristics and 16S rDNA gene sequence were combined and analyzed, and it was identified as *Bacillus* sp. X-28.

2) The physiological and biochemical results of *Kocuria* sp. X-22, *Microbacterium* sp. X-26, and *Bacillus* sp. X-28 are shown in Table 1, and the colony diagram is shown in FIG. 1.

TABLE 1

Physiological and biochemical results of strains

| | X-22 | X-26 | X-28 |
|---|---|---|---|
| Glucose fermentation | + No bubbles | + No bubbles | + No bubbles |
| Lactose fermentation | + No bubbles | − No bubbles | + No bubbles |
| Starch hydrolysis | − | − | + |
| Indole test | − | − | + |

TABLE 1-continued

Physiological and biochemical results of strains

|  | X-22 | X-26 | X-28 |
|---|---|---|---|
| Methyl red (MR) test | + | + | + |
| V.P. test | − | − | − |
| Citrate test | + | − | − |
| Hydrogen sulfide test | − | − | − |
| Gram stain | + | + | + |
| Colony morphology | coccus | bacillus | bacillus |

Embodiment 2

1. Cultivation of *Robinia pseudoacacia*

The cultivation of the *Robinia pseudoacacia* seedlings was carried out in a greenhouse at the Baima Teaching Base of Nanjing Forestry University, with an air humidity of 65%, a $CO_2$ concentration of 450 ppm and a maximum photosynthetic active radiation of 1850 µmol/(m²·s). The light intensity and time for each potted plant are ensured to be consistent every day. In order to prevent the roots of *Robinia pseudoacacia* from being rotted due to too frequent watering, the weighing method is used to add water every time to ensure that the soil water content of each pot reaches 100% of the field water holding capacity.

1) Seed soaking: The sieved black locust seeds were soaked in hot water at 60° C. (seed: water=1:3), and after natural cooling for 24 hours, the expanded seeds were selected for germination, and the remaining seeds were soaked in hot water at 80° C. The ratio is the same as above. After natural cooling for 24 hours, the expanded seeds were selected for germination. Soaking seeds in batches by successively increasing the temperature could save seeds and ensure the neat emergence of seedlings. When soaking the seeds, the cold water was changed every 12 hours to remove impurities in the water.

2) Germination: The stratification method of germination was adopted. The expanded seeds were mixed with 3 times the wet sand (being disperse once the hands are loose). To ensure the humidity of the sand, the surface of the sand was covered with a plastic wrap with some holes, and a thermometer was inserted into the sand. The sand was placed in a dark place. Germination lasted for 3~4 days, and the temperature was kept at about 20° C.

3) Into pot and thinning: The treated substrate was mixed into a pot, and seedlings with a bud length of 1 cm or more were planted. Five plants were planted in each pot, and 3 parallel treatments were set up for each treatment. After 4 weeks of growth, the seedlings were thinned, leaving 3 seedlings of the same growth in each pot.

2. Preparation of Fermentation Broth:

1) Strains of *Kocuria* sp. X-22, *Microbacterium* sp. X-26, and *Bacillus* sp. X-28 were taken, and the taken strains were activated on a nutrient agar solid medium at 35° C. for 24 hours;

2) A loop of bacterial paste of the activated *Microbacterium* sp. X-26 and *Bacillus* sp. X-28 strains was picked up with an inoculation loop and added to the LB liquid medium respectively, and *Kocuria* sp. X-22 was inoculated into NA liquid medium. The mediums were shaken at a constant temperature of 35° C., at a frequency of 200 r/min, for 24 hours to prepare a seed solution;

3) The seed solution was taken with 3% of the inoculum amount and was inoculated into liquid medium (10 g peptone, 3 g yeast powder, 5 g sodium chloride, and 1000 mL sterile water, pH 5.6). The seed solution was cultured with shaking at a temperature of 35° C., at a frequency of 200 r/min, until the $OD_{560}$ was 0.8-1.2 hours (about for 36 hours) to obtain the fermentation broth;

4) Before use, the fermentation broth obtained in step 3) was diluted with sterile water by 100 times, and then mixed in an equal volume for use.

3. Pot Experiment

Single bacteria control group (the fermentation broth dilutions of X-22, X-26, and X-28 were taken 60 mL respectively), blank control group (sterile liquid fermentation medium) and mixed bacteria group (a total of 60 mL of bacteria liquid was taken from the three fermentation bacteria broth dilutions, each 20 mL) is set. By irrigating the rhizosphere soil, the five groups were respectively added around the planted *Robinia pseudoacacia* seedlings (the first 1-4 weeks was the thinning period when no bacteria were applied, and the next 5-16 weeks is the bacteria cultivation observation period).

Three parallels were set for each treatment.

Potted plants were observed and counted for one quarter. At the 8th week, the plants were carefully dug out, the soil at the roots of the *Robinia pseudoacacia* was simply cleaned up, and the number of nodules was recorded, and then the plants were replanted into the pots. At the 16th week, the nodules were counted for the last time, and the number and weight of nodules were counted and record. The results are shown in Table 2.

TABLE 2

Results of Nodule Number, Nodule Weight and Root Dry Weight

| Processing method | Nodule Number (Pcs/plant) | | | Nodule Weight (g/Pcs) | Root Dry Weight (g) |
|---|---|---|---|---|---|
| | 8th week | 12th week | 16th week | | |
| Mixed bacteria | 0 | 3 | 7 | 0.0076 ± 0.001 | 0.57 ± 0.14 |
| X-22 | 0 | 0 | 0 | — | 0.30 ± 0.11 |
| X-26 | 0 | 0 | 0 | — | 0.29 ± 0.07 |
| X-28 | 0 | 1 | 2 | 0.0061 ± 0.001 | 0.35 ± 0.10 |
| CK | 0 | 0 | 0 | — | 0.23 ± 0.05 |

It can be seen from Table 2 that the nodules formed first in the mixed bacteria group, about between the 8th week and the 12th week, and 7 nodules had been formed by the last sampling, with a large number. Compared with the blank control group, nodule number and nodule weight of *Robinia pseudoacacia* were significantly increased after the mixture of three bacteria was applied, and the root dry weight of *Robinia pseudoacacia* treated with it also increased significantly, with an average increase of 147.83% relative to the blank control group. It can be seen that the mixed bacteria can promote the nodulation and nitrogen fixation of *Robinia pseudoacacia* and accelerate the growth and development of its roots. It is a very promising model for the configuration of promoting strains for *Robinia pseudoacacia*.

4. Promoting Experiment

According to the above method, the activated bacteria liquid is mixed and added to the surrounding of the planted *Robinia pseudoacacia* seedlings. After the first thinning, the ground diameter of the *Robinia pseudoacacia* seedlings was measured every 30 days using a vernier caliper. The seedling height of the seedlings was measured using a tape measure. On the termination day, a total of 10 upper, middle and lower leaves were selected from each pot, and the leaf areas were measured with a root scanner. The results are shown in Table 3.

TABLE 3

Promoting results

| Processing method | ground diameter (mm) | seedling height (cm) | leaf area (cm$^2$) |
|---|---|---|---|
| Mixed bacteria | 6.50 ± 0.89 | 51.93 ± 3.74 | 52.98 ± 2.69 |
| X-22 | 4.63 ± 0.34 | 44.70 ± 5.30 | 40.42 ± 3.23 |
| X-26 | 4.81 ± 0.33 | 40.57 ± 4.44 | 45.86 ± 3.54 |
| X-28 | 5.17 ± 0.43 | 41.13 ± 4.97 | 41.50 ± 2.58 |
| CK | 4.75 ± 0.38 | 40.04 ± 5.76 | 43.53 ± 2.21 |

The ground diameter is used to indicate the size of the trees, and the growing plants generally have a larger ground diameter. It can be seen from Table 3 that the ground diameter of the *Robinia pseudoacacia* seedlings treated with X-22 was lower than that of the sterile seedlings, and the ground diameter of other treatments were all higher than that of the sterile seedlings. The ground diameter of seedlings treated with mixed bacteria was significantly higher than that of sterile seedlings, increasing by 36.84% (P<0.05).

Seedling height is one of the most basic indicators of plant morphology, which can directly reflect the growth status of vegetation. In general, the seedling height of plants that grow well is relatively high. It can be seen from Table 3 that the height of the seedlings treated with various soil bacteria was higher than that of the sterile seedlings, the average seedling height was 44.58 cm, and the average increase was 11.34%. The height of the seedlings treated with the mixed bacteria was significantly higher than that of sterile seedlings, increasing by 29.7% (P<0.05).

Leaf area is one of the indicators most closely related to yield. The increase in plant yield can be directly reflected by leaf area. In general, a proper size of leaf area can make full use of light conditions without affecting photosynthesis. It can be seen from Table 3 that the leaf areas of the seedlings treated with X-22 and X-28 were lower than that of the sterile seedlings. The average leaf area is 45.19 mm2, and the average increase is 3.81%. The leaf area of seedlings treated with the mixed bacteria was significantly higher than that of sterile seedlings, increasing by 21.71% (P<0.05).

What is claimed is:

1. A method for promoting nodulation and nitrogen fixation of *Robinia pseudoacacia Robinia pseudoacacia* comprising a step of adding a mixed bacteria to a *Robinia pseudoacacia* seedling, wherein the mixed bacteria comprises *Kocuria* sp. X-22, *Microbacterium* sp. X-26, and *Bacillus* sp. X-28; and wherein the *Kocuria* sp. X-22 is preserved in China Center for Type Culture Collection with a preservation date of Apr. 8, 2019 and a preservation number of CCTCC No: M 2019237; the preservation address is Wuhan University, Wuhan, China;

the *Microbacterium* sp. X-26 is preserved in China Center for Type Culture Collection with a preservation date of Apr. 8, 2019 and a preservation number of CCTCC No: M 2019238; the preservation address is Wuhan University, Wuhan, China; and the *Bacillus* sp. X-28 is preserved in China Center for Type Culture Collection with a preservation date of Apr. 8, 2019 and the preservation number of CCTCC No: M 2019239; the preservation address is Wuhan University, Wuhan, China.

2. The method according to claim 1, wherein the mixed bacteria are respectively prepared into fermentation broths, and the respective fermentation broths are diluted and mixed and directly watered on the rhizosphere soil of *Robinia pseudoacacia* seedlings.

3. The method according to claim 2, wherein a preparation method of the fermentation broth comprises:

A) preparing strains of *Kocuria* sp. X-22, *Microbacterium* sp. X-26, and *Bacillus* sp. X-28, and activating the prepared strains on a nutrient agar solid medium at 35° C. for 24 hours;

B) picking up a loop of bacterial paste of the activated *Microbacterium* sp. X-26 and *Bacillus* sp. X-28 strains with an inoculation loop, adding the bacterial paste to an Luria-Bertani (LB) liquid medium respectively, inoculating *Kocuria* sp. X-22 into a Nutrient Agar (NA) liquid medium, and shaking the medium under a constant temperature of 35° C. with a frequency of 200_r/min for 24 hours to prepare a seed solution;

C) taking the seed solution with 3% of the inoculum amount, inoculating the taken seed solution into liquid medium, and culturing with shaking under a temperature of 35° C. with a frequency of 200 r/min for 36 hours to obtain the fermentation broth; and D) diluting the fermentation broth obtained in step C with sterile water and then mixing in an equal volume for use.

4. The method according to application of claim 3, wherein the liquid medium in step C consists of 10 g peptone, 3 g yeast powder, 5 g sodium chloride, and 1000 mL sterile water, with a pH of 5.6.

5. A method for promoting growth of *Robinia pseudoacacia* comprising a step of adding a mixed bacteria to a *Robinia pseudoacacia* seedling, wherein the mixed bacteria comprises *Kocuria* sp. X-22, *Microbocterium* sp. X-26, and *Bacillus* sp. X-28;

wherein the *Kocuria* sp. X-22 is preserved in China Center for Type Culture Collection with a preservation date of Apr. 8, 2019 and a preservation number of CCTCC No: M 2019237; the preservation address is Wuhan University, Wuhan, China;

the *Microbacterium* sp. X-26 is preserved in China Center for Type Culture Collection with a preservation date of Apr. 8, 2019 and a preservation number of CCTCC No: M 2019238; the preservation address is Wuhan University, Wuhan, China; and the *Bacillus* sp. X-28 is preserved in China Center for Type Culture Collection with a preservation date of Apr. 8, 2019 and the preservation number of CCTCC No: M 2019239; the preservation address is Wuhan University, Wuhan, China.

6. The method according to claim 5, wherein the mixed bacteria are respectively prepared into fermentation broths, and the respective fermentation broths are diluted and mixed and directly watered on the rhizosphere soil of *Robinia pseudoacacia* seedlings.

7. The method according to claim 6, wherein a preparation method of fermentation broth comprises:

A) preparing strains of *Kocuria* sp. X-22, *Microbacterium* sp. X-26, and *Bacillus* sp. X-28, and activating the prepared strains on a nutrient agar solid medium at 35° C. for 24 hours;

B) picking up a loop of bacterial paste of the activated *Microbacterium* sp. X-26 and *Bacillus* sp. X-28 strains with an inoculation loop, adding the bacterial paste to an Luria-Bertani (LB) liquid medium respectively, inoculating the *Kocuria* sp. X-22 into a Nutrient Agar (NA) liquid medium, and shaking the medium under a constant temperature of 35° C. with a frequency of 200 r/min, for 24 hours to prepare a seed solution;

C) taking the seed solution with 3% of the inoculum amount, inoculating the seed solution into liquid medium, and culturing with shaking under a temperature of 35° C. with a frequency of 200 r/min, for 36 hours to obtain the fermentation broth; and D) diluting the fermentation broth obtained in step C with sterile water, and then mixing in an equal volume for use.

8. The method according to application of claim 7, wherein the liquid medium in step C consists of 10 g peptone, 3 g yeast powder, 5 g sodium chloride, and 1000 mL sterile water, with a pH of 5.6.

\* \* \* \* \*